United States Patent
Obari et al.

(10) Patent No.: US 10,451,643 B2
(45) Date of Patent: Oct. 22, 2019

(54) SAMPLE DISPENSING DEVICE AND NOZZLE TIP FOR SAMPLE DISPENSING DEVICE

(71) Applicant: Hitachi High-Technologies Corporation, Tokyo (JP)

(72) Inventors: Kouichi Obari, Tokyo (JP); Eiji Takaya, Tokyo (JP); Takashi Otsu, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 361 days.

(21) Appl. No.: 15/308,914

(22) PCT Filed: May 15, 2015

(86) PCT No.: PCT/JP2015/063967
§ 371 (c)(1),
(2) Date: Nov. 4, 2016

(87) PCT Pub. No.: WO2015/178291
PCT Pub. Date: Nov. 26, 2015

(65) Prior Publication Data
US 2017/0059600 A1    Mar. 2, 2017

(30) Foreign Application Priority Data
May 21, 2014    (JP) ................ 2014-105121

(51) Int. Cl.
*B01L 3/02*    (2006.01)
*G01N 35/10*    (2006.01)
(Continued)

(52) U.S. Cl.
CPC ........ *G01N 35/1011* (2013.01); *B01L 3/0275* (2013.01); *G01N 1/00* (2013.01);
(Continued)

(58) Field of Classification Search
CPC .... B01L 3/0275; B01L 3/0279; B01L 3/0282; B01L 2200/04; G01N 35/1011;
(Continued)

(56) References Cited

U.S. PATENT DOCUMENTS 4,936,835 A * 6/1990 Haaga ................ A61B 10/0233
604/265
5,049,138 A * 9/1991 Chevalier ............. A61L 29/041
604/265
(Continued)

FOREIGN PATENT DOCUMENTS

JP    07-191018 A    7/1995
JP    08-060726 A    3/1996
(Continued)

OTHER PUBLICATIONS

International Search Report of PCT/JP2015/063967 dated Aug. 11, 2015.
(Continued)

*Primary Examiner* — Brian R Gordon
(74) *Attorney, Agent, or Firm* — Mattingly & Malur, PC (57) ABSTRACT

The sample dispensing device sucks a liquid sample from a predetermined container and then discharges the sample to another container. The sample dispensing device includes a nozzle tip that sucks and holds the sample; a dispensing nozzle to which the nozzle tip can be detachably attached via a fitting part; a dispensing nozzle position control means that controls the position of the dispensing nozzle with respect to the predetermined container and the other container; a nozzle tip removing means that removes the nozzle tip from the dispensing nozzle; and a discarding box into which water can be supplied, and in which the nozzle tip removed from the dispensing nozzle is discarded. The nozzle tip is made of a water-soluble material, and after being removed from the
(Continued)

dispensing nozzle by the nozzle tip removing means, the nozzle tip is dissolved by water in the discarding box.

12 Claims, 5 Drawing Sheets

(51) Int. Cl.
*G01N 1/00* (2006.01)
*G01N 35/00* (2006.01)

(52) U.S. Cl.
CPC ........ *G01N 35/10* (2013.01); *B01L 2200/026* (2013.01); *B01L 2300/12* (2013.01); *G01N 2035/00346* (2013.01); *G01N 2035/00534* (2013.01); *G01N 2035/103* (2013.01)

(58) Field of Classification Search
CPC .... G01N 1/00; G01N 35/10; G01N 2035/103; G01N 2035/00534; G01N 2035/00346
USPC .......................................... 422/511, 524, 525
See application file for complete search history.

(56) References Cited

U.S. PATENT DOCUMENTS

| | | | | |
|---|---|---|---|---|
| 5,401,257 | A * | 3/1995 | Chevalier, Jr. .... | A61M 25/0017 604/265 |
| 5,514,112 | A * | 5/1996 | Chu ...................... | A61M 27/00 604/265 |
| 5,603,698 | A * | 2/1997 | Roberts .................... | A61F 2/95 604/104 |
| 5,860,916 | A * | 1/1999 | Pylant ................. | A61M 3/0258 600/114 |
| 5,931,776 | A * | 8/1999 | Dotolo ................ | A61M 3/0283 600/184 |
| 6,071,300 | A * | 6/2000 | Brenneman ......... | A61B 17/0057 604/265 |
| 6,332,877 | B1 * | 12/2001 | Michels ................ | A61L 29/043 604/263 |
| 6,673,058 | B2 * | 1/2004 | Snow ................... | A61J 15/0023 128/898 |
| 6,984,224 | B2 * | 1/2006 | McKittrick ......... | A61M 1/0084 604/270 |
| 7,004,962 | B2 * | 2/2006 | Stinson ............. | A61B 17/12022 604/265 |
| 7,048,710 | B1 * | 5/2006 | Cragg ................ | A61B 17/0057 604/15 |
| 7,611,479 | B2 * | 11/2009 | Cragg ................ | A61B 17/0057 604/11 |
| 2011/0178286 | A1 | 7/2011 | Bessetti et al. | |
| 2012/0309104 | A1 * | 12/2012 | Uematsu ................ | G01N 35/10 436/174 |
| 2017/0113217 | A1 * | 4/2017 | Ledden ................ | B01L 3/0293 |
| 2017/0136456 | A1 * | 5/2017 | Chen ..................... | B01L 3/5085 |

FOREIGN PATENT DOCUMENTS

| | | |
|---|---|---|
| JP | 3410018 B2 | 5/2003 |
| JP | 2003-294771 A | 10/2003 |
| JP | 2007-064706 A | 3/2007 |
| JP | 2007-139470 A | 6/2007 |
| JP | 2012-021805 A | 2/2012 |
| JP | 2013-522578 A | 6/2013 |
| WO | 2011/091237 A1 | 7/2011 |

OTHER PUBLICATIONS

Extended European Search Report received in corresponding European Application No. 15795553.5 dated Jan. 5, 2018.

* cited by examiner

SAMPLE DISPENSING DEVICE AND NOZZLE TIP FOR SAMPLE DISPENSING DEVICE

TECHNICAL FIELD

The present invention relates to a sample dispensing apparatus and especially relates to a sample dispensing apparatus that dispenses a sample such as blood or urine which has been collected for testing into another container using a disposable nozzle tip.

BACKGROUND ART

To take a necessary amount of a sample such as blood or urine for analysis or testing from a container in which the sample has been collected (a mother sample container) into a test container (a daughter sample container), a sample dispensing apparatus in which a disposable nozzle tip sucks the sample in the mother sample container and discharges the sample to the daughter sample container is known.

An example of known sample dispensing apparatuses is a sample dispensing apparatus described in PTL 1. PTL 1 discloses "a sample dispensing apparatus having a main transfer line for transferring a mother rack containing a sample to be dispensed, a dispensing station which is placed along the main transfer line and which dispenses the sample from one rack to another rack and a daughter rack supply device which supplies a daughter rack holding a container for receiving the sample to be dispensed to the dispensing station, characterized in that the mother rack and the daughter rack treated at the dispensing station are together moved to the main transfer line and transferred, a waiting area where the mother rack and the daughter rack treated at the dispensing station wait before being moved to the main transfer line is provided, a mother rack pathway where the mother rack brought into from the main transfer line is placed and a daughter rack pathway where the daughter rack transferred from the daughter rack supply device is placed are provided at the dispensing station and the mother rack which has passed through the mother rack pathway and the daughter rack which has passed through the daughter rack pathway are aligned in the waiting area".

In the sample dispensing apparatus of PTL 1, an unused nozzle tip is fitted to a dispensing nozzle provided on a dispensing head, removed from the dispensing nozzle after being used for dispensing a sample and discarded.

In such a sample dispensing apparatus, after a sample in one mother sample container is dispensed to a daughter sample container, the nozzle tip is removed from the dispensing nozzle and is dropped into and collected in a discarding box in order to prevent the sample from contaminating another mother sample container. Then, after the sample treatment of the day, the discarding box is removed from the sample dispensing apparatus and discarded according to the management method of the facility.

CITATION LIST

Patent Literature

PTL 1: U.S. Pat. No. 3,410,018

SUMMARY OF INVENTION

Technical Problem

Figure 6:
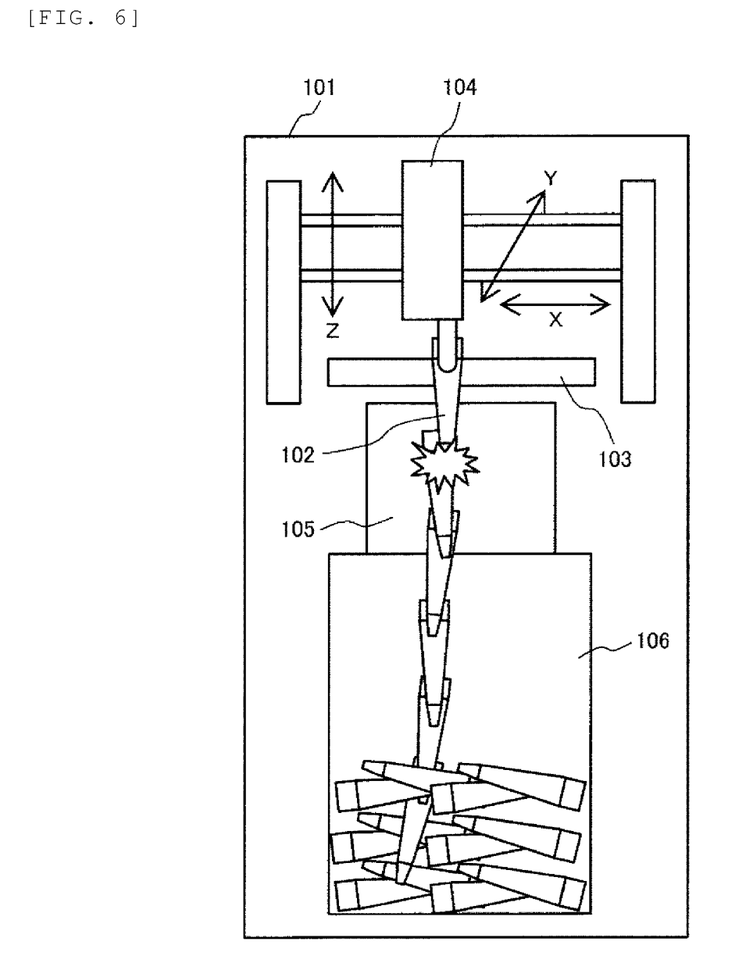
FIG. 6 A figure illustrating a part of a conventional sample dispensing apparatus (when a discarding error occurs).

As described above, a disposable nozzle tip after dispensing a sample is removed from the fitting part of the dispensing nozzle and dropped into and collected in the discarding box. However, depending on the state of dropping, the end of a nozzle tip discarded sticks in or overlaps with the hole of the nozzle tip which has been discarded before, as shown in FIG. 6, and when this is repeated in the vertical direction, a nozzle tip sticks out from the discarding box before the discarding box becomes full. This state adversely affects the discarding operation and causes a trouble of the apparatus in which the tip discarded next does not drop into the discarding box.

The ends of the nozzle tips generally have a conical shape. Waste which has a pointed end and which carries a high risk of an accident of piercing or the like, such as injection needles, is required to be discarded in a resin container or the like. The treatment requires certain procedures and costs. Because nozzle tips made of a resin or the like are not as pointed as injection needles, the nozzle tips are generally collected in a discarding bag made of plastic as biohazardous waste and burned after autoclave treatment. However, as the volume to be dispensed has become very small, a shape with a fine tip has been introduced, and a risk of piercing through a plastic bag has become high. When nozzle tips are discarded using a plastic bag as in the conventional manner, it is preferable in view of the safety that the tips are not sharp. Moreover, also when nozzle tips are discarded using a plastic bag, because the nozzle tips have the shape of hollow pipe, the space filling rate is low. That the volume of the waste can be reduced is highly advantageous for the operation.

Thus, an object of the invention is to provide a sample dispensing apparatus which is suitable for discarding a nozzle tip and reducing the volume thereof when a used nozzle tip is discarded.

Moreover, another object of the invention is to provide a nozzle tip for a sample dispensing apparatus which is suitable for discarding a nozzle tip and reducing the volume thereof when a used nozzle tip is discarded.

Solution to Problem

The invention relates to a sample dispensing apparatus that sucks a liquid sample from a predetermined container and then discharges the sample to another container. The sample dispensing apparatus: has a nozzle tip that sucks and holds the sample; a dispensing nozzle to which the nozzle tip can be attached and detached through a fitting part; dispensing nozzle position control means that controls the position of the dispensing nozzle relative to the predetermined container and the other container; nozzle tip removing means that removes the nozzle tip from the dispensing nozzle; and a discarding box into which water can be supplied and into which the nozzle tip removed from the dispensing nozzle is discarded: and is characterized in that the nozzle tip is made of a water-soluble material and is dissolved in the water in the discarding box after being removed from the dispensing nozzle by the nozzle tip removing means.

Moreover, the invention relates to a sample dispensing apparatus that sucks a liquid sample from a predetermined container and then discharges the sample to another container. The sample dispensing apparatus: has a nozzle tip that sucks and holds the sample; a dispensing nozzle to which the nozzle tip can be attached and detached through a fitting part; dispensing nozzle position control means that controls the position of the dispensing nozzle relative to the predetermined container and the other container; nozzle tip removing means that removes the nozzle tip from the dispensing nozzle; and a discarding box in which a chemical liquid can be contained and into which the nozzle tip removed from the dispensing nozzle is discarded: and is characterized in that the nozzle tip is dissolved in the chemical liquid in the discarding box after being removed from the dispensing nozzle by the nozzle tip removing means.

Furthermore, the invention relates to a nozzle tip for a sample dispensing apparatus used for a sample dispensing apparatus that sucks a liquid sample from a predetermined container and then discharges the sample to another container, and the nozzle tip for a sample dispensing apparatus is characterized by having a shape that can be attached to and detached from a dispensing nozzle of the sample dispensing apparatus through a fitting part provided on the dispensing nozzle and being made of a water-soluble resin that can be formed by heat melting.

Advantageous Effects of Invention

According to the invention, a sample dispensing apparatus which does not easily cause a trouble of the apparatus when a used nozzle tip is discarded and in which a nozzle tip can be discarded safely and easily can be achieved.

Moreover, according to the invention, a nozzle tip for a sample dispensing apparatus which does not easily cause a trouble of the apparatus when a used nozzle tip is discarded and in which a nozzle tip can be discarded safely and easily can be achieved.

Problems, structures and effects except for those described above are clarified by the description of embodiments below.

DESCRIPTION OF EMBODIMENTS

Examples of the invention are explained below using the drawings.

Example 1

Figure 1:
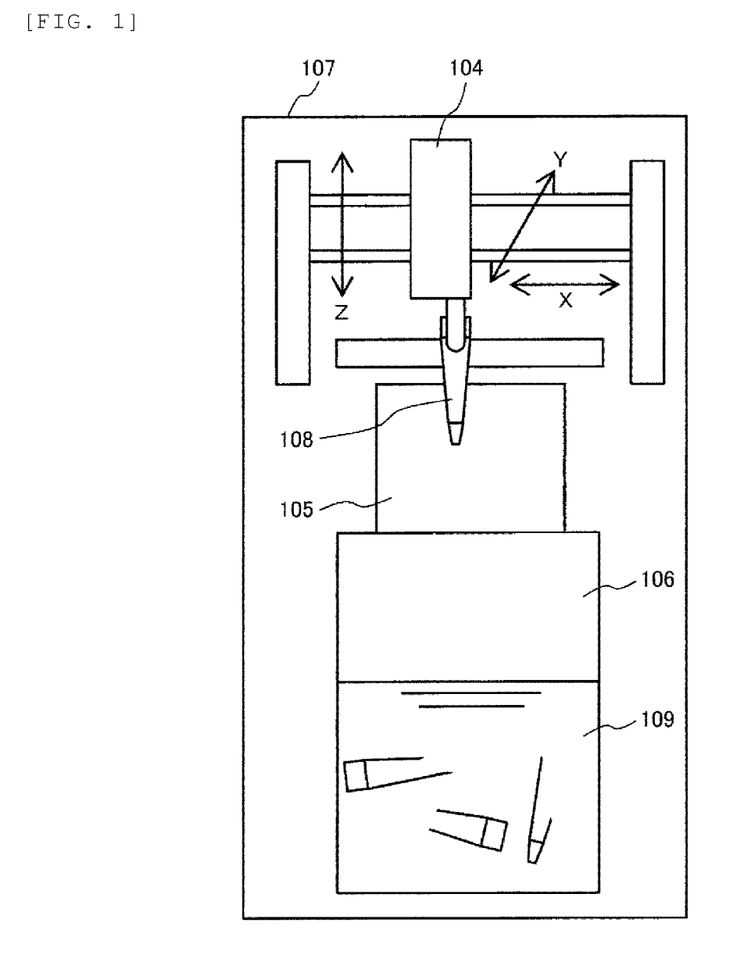
FIG. 1 figure illustrating a part of the sample dispensing apparatus according to an embodiment of the invention.

The sample dispensing apparatus of an Example of the invention is illustrated in FIG. 1. Also, a conventional sample dispensing apparatus is illustrated in FIG. 6 for comparison. FIG. 6 shows how a discarding error of a nozzle tip occurs in the conventional sample dispensing apparatus.

The conventional sample dispensing apparatus and the sample dispensing apparatus of the invention are both sample dispensing apparatuses in which a sample that is mostly liquid, such as blood or urine, is sucked from a predetermined container to which the sample has been collected (a mother sample container) and then discharged to one or more other test containers (daughter sample container(s)) to take a necessary amount for analysis or testing. The sample dispensing apparatuses can dispense not only a liquid sample such as blood or urine but also liquid obtained by dissolving a solid sample such as a skin piece or hair in a chemical liquid (chemical).

First, the structure around a dispensing nozzle 104 and a discarding box 106 of a conventional sample dispensing apparatus 101 is explained using FIG. 6. A disposable nozzle tip 102 is formed in a shape which fits a fitting part provided on the dispensing nozzle 104 and has a structure which can be attached to and detached from the dispensing nozzle 104 through the fitting part of the dispensing nozzle 104.

An unused disposable nozzle tip 102 is attached to the dispensing nozzle 104 through the fitting part. Then, after the disposable nozzle tip 102 sucks a liquid sample from a predetermined container containing the sample (a mother sample container) at a dispensing part of the sample dispensing apparatus (not shown in the figure), the dispensing nozzle 104 is moved to the position of one or more other test containers (daughter sample container (s)) while keeping the liquid sample sucked in the disposable nozzle tip 102, and the disposable nozzle tip 102 discharges the sucked liquid sample to the test container (s) (the daughter sample container (s)). The dispensing nozzle 104 is moved by dispensing nozzle position control means while the position thereof in the X direction, the Y direction and the Z direction relative to the mother sample container, the daughter sample container (s) and the discarding box 106 is controlled by a control device (not shown in the figure).

The dispensing nozzle 104 which has finished sucking the liquid sample from the mother sample container and discharging the sample to the daughter sample container (s), namely the dispensing nozzle 104 after dispensing, is moved to above the discarding box 106 by the dispensing nozzle position control means. Then, the disposable nozzle tip 102 attached to the fitting part provided on the dispensing nozzle 104 is removed from the fitting part of the dispensing nozzle 104 by a tip removing device 103, passes through a discarding path 105, drops into the discarding box 106 and is collected in the discarding box 106.

Polypropylene or the like is generally used as the material of the disposable nozzle tip 102 of the conventional sample dispensing apparatus 101. Polypropylene is multipurpose plastic and is a highly strong, hardly hygroscopic and chemically resistant material.

Here, as shown in FIG. 6, depending on the state of dropping of the disposable nozzle tip 102 to the discarding box 106, the end of the nozzle tip discarded sticks in or overlaps with the hole of a nozzle tip which has been discarded before, and when this is repeated in the vertical direction, a nozzle tip 102 sticks out from the discarding box 106 before the discarding box 106 becomes full. As a result, a trouble of the apparatus in which the operation of discarding the following disposable nozzle tips 102 cannot be conducted is caused.

Next, the structure around the dispensing nozzle 104 and the discarding box 106 of a sample dispensing apparatus 107 in the Example is explained using FIG. 1.

The sample dispensing apparatus 107 of the Example has the almost same structure as that of the conventional sample dispensing apparatus 101 illustrated in FIG. 6 in that a disposable nozzle tip 108 can be attached to and detached from the fitting part provided on the dispensing nozzle 104 and that dispensing nozzle position control means that controls the position of the dispensing nozzle 104 in the X direction, the Y direction and the Z direction is provided.

The sample dispensing apparatus 107 of the Example is different from the conventional sample dispensing apparatus 101 in that the disposable nozzle tip 108 is made of water-soluble plastic (resin) which can be formed by heat melting while the disposable nozzle tip 102 of the conventional sample dispensing apparatus 101 is made of multipurpose plastic such as polypropylene. As the water-soluble plastic (resin) which can be formed by heat melting, for example a resin containing polyvinyl alcohol as the main component is used.

As such a water-soluble material, for example, resin materials containing a oxyalkylene group-containing vinyl alcohol-based polymer described in U.S. Pat. No. 4,618,648, JP-A-59-155408, JP-A-01-158016, JP-A-07-316379 and the like can be used. When such a material is used, a nozzle tip having excellent water dissolution rate and excellent water dissolution removal property can be formed.

Moreover, while the disposable nozzle tips 102 discarded are collected in the discarding box 106 of the conventional sample dispensing apparatus 101, the discarding box 106 of the sample dispensing apparatus 107 of the Example has a structure into which water can be supplied and in which water 109 can be stored.

The disposable nozzle tip 108 of the sample dispensing apparatus 107 of the Example is made of a water-soluble material as described above, and water is contained in the discarding box 106. Thus, after dispensing a sample, the disposable nozzle tip 108 is removed from the dispensing nozzle 106 by the tip removing device 103, passes through the discarding path 105, drops into the discarding box 106 containing the water 109, is dissolved in the water 109 and is discarded.

As described above, according to the sample dispensing apparatus 107 of the Example, water-soluble plastic (resin) which can be formed by heat melting is used as the material of the disposable nozzle tip 108, and the discarding box 106 contains the water 109. Thus, because the disposable nozzle tip 108 discarded into the discarding box 106 is dissolved in the discarding box 106, the disposable nozzle tip 108 does not overlap with another one in the discarding box 106, and a trouble of the apparatus due to the discarding state of the disposable nozzle tip 108 can be prevented.

In addition, because the disposable nozzle tips 108 discarded are dissolved in the sample dispensing apparatus 107, the tips discarded are less likely to pile up, and the volume of the waste can be made compact. A discarding bag of the used disposable nozzle tips 108, namely a packaging material or a discarding container, is not necessary, and the collection thereof is not necessary, either.

Furthermore, because the disposable nozzle tips 108 are dissolved, the tips discarded do not make a hole in the discarding bag or stick into a finger.

Here, when the disposable nozzle tips 108 are not completely dissolved but are partially dissolved, the disposable nozzle tips 108 do not pile up, and discarding errors of the nozzle tips, namely the trouble of the apparatus, can be reduced.

As described above, water-soluble plastic (resin) which can be formed by heat melting is used as the material of the disposable nozzle tips 108 of the sample dispensing apparatus 107 of the Example. However, depending on the kind or the properties of the sample and the contents of the analysis or the testing of the purpose, a material which has other properties such as excellent biodegradability, property of not generating poisonous gas when being burned and excellent chemical resistance in addition to water solubility can also be selected.

Example 2

Figure 2A:
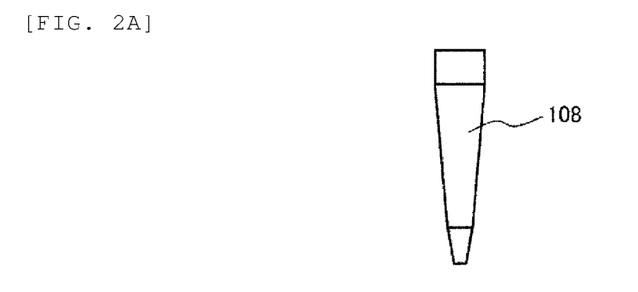
FIG. 2A A figure illustrating the nozzle tip for a sample dispensing apparatus according to an embodiment of the invention.
Figure 2B:
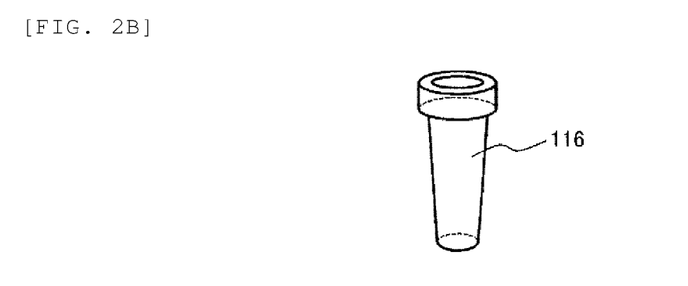
FIG. 2B A figure illustrating the sample cup according to an embodiment of the invention.
Figure 2C:
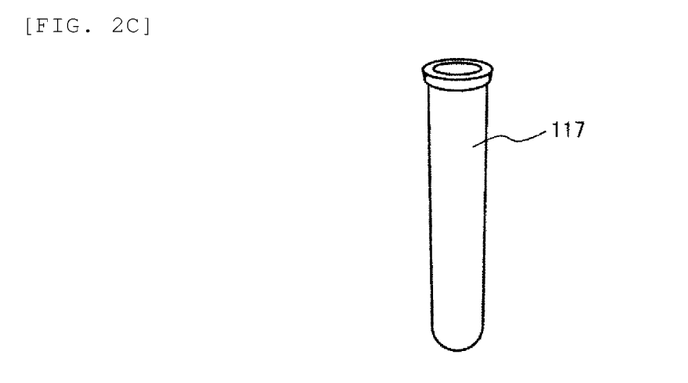
FIG. 2C A figure illustrating the test tube (blood collection tube) according to an embodiment of the invention.

Modified examples of the disposable nozzle tip 108 of the sample dispensing apparatus 107 explained in Example 1 are illustrated in FIG. 2A to FIG. 2C. In Example 1, an example in which the disposable nozzle tips 108 of the sample dispensing apparatus 107 are made of water-soluble plastic (resin) which can be formed by heat melting and are discarded while being dissolved in the water 109 in the discarding box 106 has been explained. When disposable sample cups 116 or disposable test tubes (blood collection tubes) 117 used for similar analysis or testing are made of water-soluble plastic (resin) which can be formed by heat melting for example, the disposable sample cups 116 or the disposable test tubes (blood collection tubes) 117 can be dissolved in water for discarding as the disposable nozzle tips 108 of Example 1 and thus are less likely to pile up. Thus, the volume of the waste can be made compact. A discarding bag of the disposable nozzle tips 108, the sample cups 116 and the test tubes (blood collection tubes) 117 after use, namely a packaging material or a discarding container, is not necessary, and the collection thereof is not necessary, either.

Example 3

Figure 3:
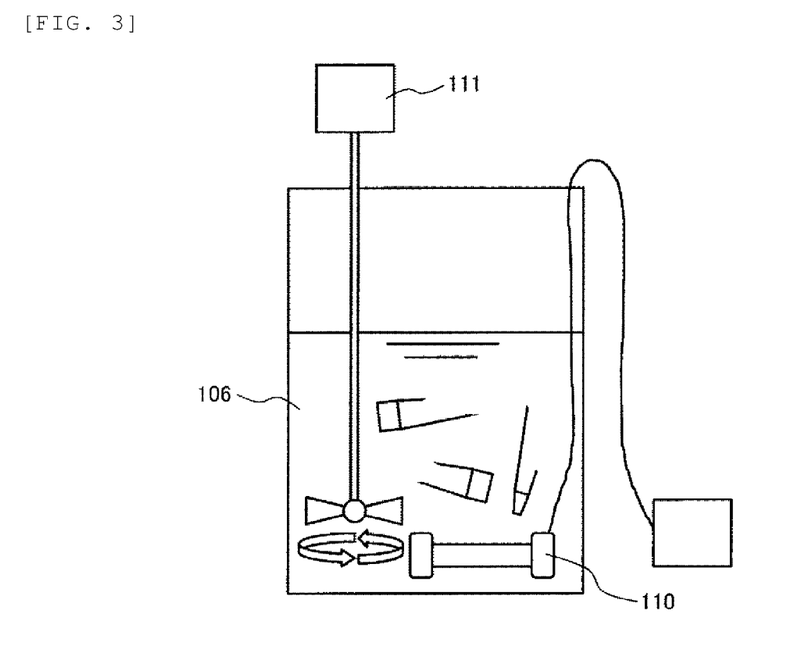
FIG. 3 A figure illustrating the discarding box according to an embodiment of the invention.

The sample dispensing apparatus of another Example of the invention is illustrated in FIG. 3. In the Example, a heater 110 is further provided as temperature control means that controls the temperature of the water in the discarding box 106 of the sample dispensing apparatus 107 of Example 1. Moreover, a stirring device 111 that stirs the water 109 inside is provided in the discarding box 106.

In other words, the discarding box 106 has a structure which can contain water, which is liquid, as explained in Example 1, and the disposable nozzle tip 108 is made of a water-soluble material. Thus, by heating the water in the discarding box 106 using the heater 110, the water can be made warm water, and the dissolution period can be controlled. Some kinds of the water-soluble plastic (resin) which can be formed by heat melting explained in Example 1 have a property that the dissolution period becomes shorter when being soaked in warm water. Thus, by providing the heater 110 in the discarding box 106, the dissolution period of the disposable nozzle tip 108 in the water 109 can be shortened.

Specifically, when the disposable nozzle tip 108 after use is sterilized and dissolved by soaking in hot water of 95° C. or higher and further soaking in hot water containing a disinfectant, efficient treatment can be conducted easily.

Moreover, by adding the stirring device 111 that stirs the water in the discarding box 106, the dissolution of the disposable nozzle tip 108 in the water 109 can be promoted.

As shown in FIG. 3, by providing both of the heater 110 and the stirring device 111 in the discarding box 106, the dissolution of the disposable nozzle tip 108 in the water 109 can be further promoted by the synergistic effect thereof.

Example 4

Figure 4:
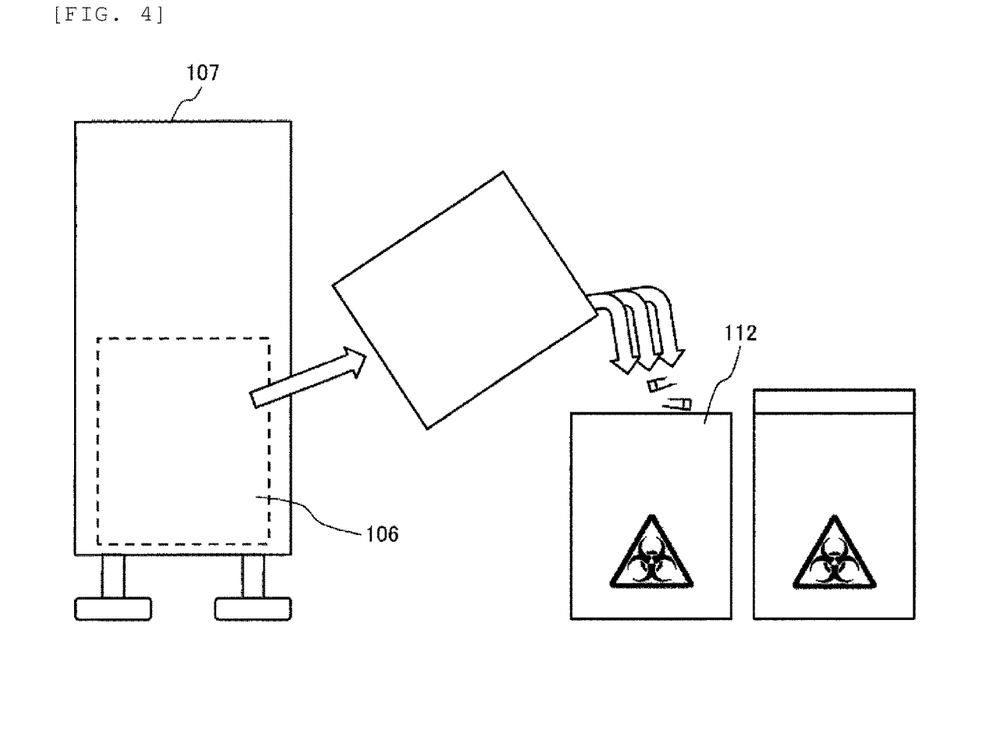
FIG. 4 A figure illustrating the method for discarding waste according to an embodiment of the invention.

An example of the method for discarding the waste in which the disposable nozzle tips 108, the disposable sample cups 116 or the disposable test tubes (blood collection tubes)

117 explained in Example 1 to Example 3 are dissolved is illustrated in FIG. 4. As in FIG. 4, when the waste (waste water) in which the disposable nozzle tips 108, the disposable sample cups 116 or the disposable test tubes (blood collection tubes) 117 discarded are completely or partially dissolved is discarded, the discarding box 106 is removed from the sample dispensing apparatus 107, and the waste is moved to a waste container 112 according to the waste management method of the facility to which the sample dispensing apparatus 107 is introduced. The waste is stored in a waste storage or the like and then treated in a waste treatment equipment (facility).

Here, also when the disposable nozzle tips 108, the disposable sample cups 116 or the disposable test tubes (blood collection tubes) 117 discarded are not completely dissolved in the discarding box 106, the disposable nozzle tips 108, the disposable sample cups 116 or the disposable test tubes (blood collection tubes) 117 may be dissolved completely in the waste container 112 during the storage in the waste storage.

Example 5

Figure 5:
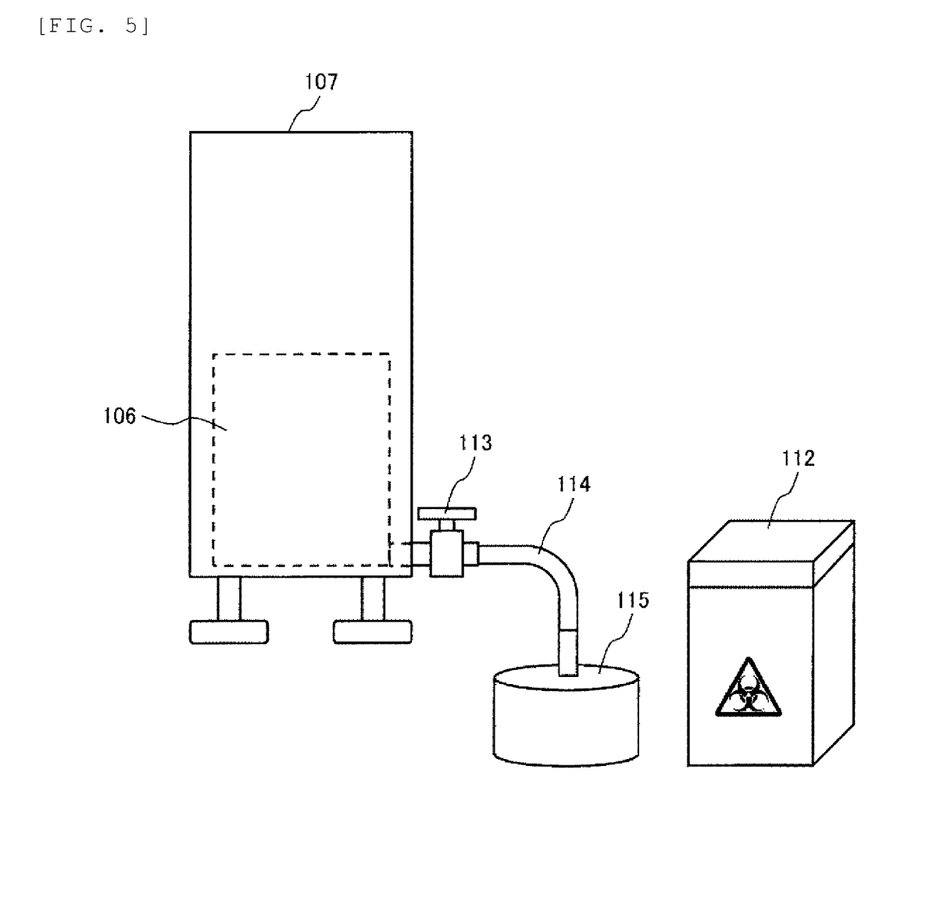
FIG. 5 A figure illustrating the method for discarding waste according to an embodiment of the invention.

Another example of the method for discarding the waste in which the disposable nozzle tips 108, the disposable sample cups 116 or the disposable test tubes (blood collection tubes) 117 explained in Example 1 to Example 3 are dissolved is illustrated in FIG. 5.

As shown in FIG. 5, in the sample dispensing apparatus 107 of the Example, the discarding box 106 is connected to a drainage way 115 by a drainage hose 114 through a cock 113, which is a valve, that is, the discarding box 106 is connected to a waste water treatment equipment (facility) of the facility to which the sample dispensing apparatus 107 is introduced. By opening the cock 113, the waste (waste water) in which the disposable nozzle tips 108, the disposable sample cups 116 or the disposable test tubes (blood collection tubes) 117 are dissolved in the discarding box 106 is drained to the waste water treatment equipment (facility).

Although the treatment is conducted according to the standard and the method for the waste management of the facility to which the sample dispensing apparatus 107 is introduced, when direct drainage of the waste (waste water) is allowed in the facility, the cock 113 of the discarding box 106 is opened to discard the waste (waste water) in which the disposable nozzle tips 108 or the like are dissolved to the drainage way 115 or the waste container 112 through the drainage hose 114.

In this manner, the disposable nozzle tips 108 discarded can be dissolved in the apparatus without opening the apparatus cover of the sample dispensing apparatus 107 and treated as waste. Also, because the disposable nozzle tips 108 are dissolved in the sample dispensing apparatus 107, the tips discarded do not make a hole in the discarding bag or stick into a finger.

Furthermore, the discarding box 106 may have a disposer that crushes the nozzle tips 108 which slightly maintain their shapes. The disposer is provided before the cock 113 and the drainage hose 114 and can crush the waste transferred to the drainage way 115 or the waste container 112 into small pieces. This can prevent the drainage path from being clogged and can further reduce the burden of the operator of the waste treatment.

Example 6

In the sample dispensing apparatuses explained in Example 1 and Example 3 to Example 5, the conventional disposable nozzle tip 102, namely a nozzle tip made using multipurpose plastic such as polypropylene, can be used instead of the disposable nozzle tip 108 made using water-soluble plastic (resin) which can be formed by heat melting, and the structure may be composed as a structure in which a chemical liquid (chemical) can be contained in the discarding box 106 instead of supplying the water 109 into the discarding box 106. Also, by supplying a chemical liquid (chemical) which dissolves the disposable nozzle tip 102 into the discarding box 106, the disposable nozzle tip 102 can be dissolved in the chemical liquid (chemical) in the discarding box 106. Thus, similar effects to those of the sample dispensing apparatuses of Example 1 and Example 3 to Example 5 can be obtained.

As the chemical liquid (chemical) which dissolves polypropylene which is the material of the disposable nozzle tip 102, for example, furfural (($C_4H_3O$)CHO) is used.

According to the Example, the disposable nozzle tip 102 can be dissolved in the chemical liquid (chemical) in the discarding box 106 as in Example 1 and Example 3 to Example 5. Thus, the disposable nozzle tip 102 does not overlap with another one in the discarding box 106, and a trouble of the apparatus due to the discarding state of the disposable nozzle tip 102 can be prevented.

Moreover, because the disposable nozzle tips 102 discarded are dissolved in the apparatus, the tips discarded are less likely to pile up, and the volume of the waste can be made compact. A discarding bag of the used disposable nozzle tips 108, namely a packaging material or a discarding container, is not necessary, and the collection thereof is not necessary, either.

Furthermore, because the disposable nozzle tips 102 are dissolved, the tips discarded do not make a hole in the discarding bag or stick into a finger.

In the Example, however, the disposable nozzle tips 102 made of multipurpose plastic such as polypropylene, which is the same material as the conventional material, are dissolved in the chemical liquid (chemical) in the discarding box 106. Therefore, it is necessary for example to make the discarding box 106 with a chemically resistant material, to compose the discarding box 106 as a closed structure depending on the properties of the chemical liquid (chemical) used or to provide a ventilation equipment.

The invention is not limited to the Examples described above and includes various modified examples. For example, the Examples have been explained above in detail to explain the invention simply but are not limited to those having all the components explained. Also, some of the components of an Example can be substituted for components of another Example, and a component of an Example can be added to the components of another Example. Moreover, some of the components of an Example can be deleted or substituted for another component, or another component can be added.

REFERENCE SIGNS LIST

101 . . . (Conventional) sample dispensing apparatus,
102 . . . disposable nozzle tip (a conventional product),
103 . . . tip removing device,
104 . . . dispensing nozzle,
105 . . . discarding path,
106 . . . discarding box,
107 . . . sample dispensing apparatus (a product of the invention),
108 . . . disposable nozzle tip (a product of the invention),
109 . . . water, 110 . . . heater,
111 . . . stirring device,
112 . . . waste container,
113 . . . cock,
114 . . . drainage hose,
115 . . . drainage way,
116 . . . disposable sample cup and
117 . . . disposable test tube (blood collection tube).

The invention claimed is:

1. A sample dispensing apparatus that sucks a liquid sample from a predetermined container and then discharges the sample to another container, the sample dispensing apparatus comprising:
a nozzle tip that sucks and holds the sample;
a dispensing nozzle to which the nozzle tip is detachably attached through a fitting part of the nozzle; and
a discarding box configured to have a liquid supplied therein and configured to receive the nozzle tip in a state where the nozzle tip is detached from the dispensing nozzle,
wherein the nozzle tip is made of a material which is soluble in the liquid and is configured to be dissolved in the liquid in the discarding box, and
wherein the discarding box has stirring means that stirs the liquid in the discarding box.

2. The sample dispensing apparatus according to claim 1, wherein the material of the nozzle tip is a water-soluble resin.

3. The sample dispensing apparatus according to claim 1, wherein the discarding box has a heater configured to control the temperature of the liquid in the discarding box.

4. The sample dispensing apparatus according to claim 1, comprising a valve and a drain hose connected through the valve to the discarding box at a first end and a second end of the drain hose is configured to be connected to a waste liquid treatment equipment.

5. The sample dispensing apparatus according to claim 1, wherein the material of the nozzle tip is soluble in water as the liquid.

6. The sample dispensing apparatus according to claim 1, wherein the material of the nozzle tip is soluble in furfural as the liquid.

7. A sample dispensing apparatus that sucks a liquid sample from a predetermined container and then discharges the sample to another container, the sample dispensing apparatus comprising:
a nozzle tip that sucks and holds the sample;
a dispensing nozzle to which the nozzle tip is detachably attached through a fitting part of the nozzle; and
a discarding box configured to have a liquid supplied therein and configured to receive the nozzle tip in a state where the nozzle tip is detached from the dispensing nozzle,
wherein the nozzle tip is made of a material which is soluble in the liquid and is configured to be dissolved in the liquid in the discarding box, and
wherein the discarding box has a heater configured to control the temperature of the liquid in the discarding box.

8. The sample dispensing apparatus according to claim 7, wherein the discarding box has a stirring device that stirs the liquid in the discarding box.

9. The sample dispensing apparatus according to claim 7, comprising a valve and a drain hose connected through the valve to the discarding box at a first end and a second end of the drain hose is configured to be connected to a waste liquid treatment equipment.

10. The sample dispensing apparatus according to claim 7, wherein the material of the nozzle tip is soluble in water as the liquid.

11. The sample dispensing apparatus according to claim 7, wherein the material of the nozzle tip is soluble in furfural as the liquid.

12. The sample dispensing apparatus according to claim 7, wherein the material of the nozzle tip is a water-soluble resin.

* * * * *